United States Patent [19]
Freitag

[11] Patent Number: 5,601,593
[45] Date of Patent: Feb. 11, 1997

[54] STENT FOR PLACEMENT IN A BODY TUBE

[75] Inventor: Lutz Freitag, Hemer, Germany

[73] Assignee: Willy Rüsch AG, Kernen, Germany

[21] Appl. No.: 517,162

[22] Filed: Aug. 18, 1995

[30] Foreign Application Priority Data

Mar. 6, 1995 [DE] Germany .................. 195 08 805.0

[51] Int. Cl.⁶ .................................................. A61M 29/00
[52] U.S. Cl. ........................ 606/198; 606/191; 606/195; 623/1; 623/12
[58] Field of Search ..................... 606/194, 195, 606/197, 198; 623/1, 12; 148/402, 403; 604/96, 104

[56] References Cited

U.S. PATENT DOCUMENTS 5,197,978  3/1993  Hess ........................................ 606/194
5,201,901  4/1993  Harada et al.
5,383,892  1/1995  Cardon et al. ......................... 606/198

FOREIGN PATENT DOCUMENTS 4219949  12/1993  Germany .
4240177   6/1994  Germany .
4301181   7/1994  Germany .
9116881   8/1994  Germany .

Primary Examiner—Michael Powell Buiz
Assistant Examiner—Kevin Truong
Attorney, Agent, or Firm—Friedrich Kueffner

[57] ABSTRACT

A stent for placement in a body tube includes a flexible support structure of wires, wherein the wires are of a material having a shape memory function. The support structure of the stent is composed of wires which have different shape memories. In a method for changing the configuration of a stent of the above-described type which has been placed in a body tube, the stent is subjected over at least portions thereof to a specific application of heat or cold in order to influence the restoring force and/or the geometric shape.

10 Claims, 1 Drawing Sheet

STENT FOR PLACEMENT IN A BODY TUBE

BACKGROUND OF THE INVENTION

1. Field of the Invention

The present invention relates to a stent for placement in a body tube. The stent includes a flexible support structure of wires, wherein the wires are of a material having a shape memory function.

The present invention also relates to a method for changing the configuration of a stent of the above-described type which has been placed in a body tube.

2. Description of the Related Art

Stents are hollow cylindrical spacer members which are implanted operatively, percutaneously or endoscopically in order to keep tubes in the body open, for example, the trachea, bronchial tubes, esophagus, biliary duct, urinary passage, blood vessels and the like.

Such stents must have a restoring force for withstanding an external compression which is caused, for example, by a tumor or a lymph node, or a vessel stricture resulting from cauterization, sclerosis or cicatrization.

Stents of different configurations and construction are known for keeping open a stenosis. The stents may be of plastic construction, metal construction or hybrid construction. Many stents have fixed end diameters and are self-expanding, as disclosed in DE-GM 91 16 881 or DE-OS 42 40 177.

In other embodiments, the diameter of the stent can be changed and adapted to the respective anatomical situation by suitable means, for example, balloons or spreaders. Such a stent is known from U.S. Pat. No. 5,201,901.

Also known in the art are stents of a so called shape memory alloy, for example, from DE-OS 42 19 949 and. For example, nitinol is a shape memory alloy. Nitinol has two distinct states which occur depending on the temperature. After a pretreatment, nitinol is martensitic, i.e., plastically deformable, in the cold state and does not have a relevant elastic restoring force. After heating, nitinol changes into an austenitic, elastic state.

The shape memory property is utilized for the self-expansion of various stents.

The restoring force, i.e., the force with which the stent counteracts a compression, depends on the construction and the thickness of the wires. There are also stents of thermoplastic synthetic material, such as polyurethane, in which the restoring force depends on the material thickness.

Depending on their construction and the type of application, the known stents operate satisfactorily. However, it is desirable to be able to change the restoring force of a stent in vivo, i.e., after placement in the body, in order to be able to adapt to different conditions, as they occur, for example, as a result of the growth of a tumor.

SUMMARY OF THE INVENTION

Therefore, it is the primary object of the present invention to provide a stent of the above-described type whose restoring force can be changed after having been placed in the body.

It is another object of the present invention to provide a method for changing the configuration of a stent placed in a body tube in a simple manner.

In accordance with the present invention, the support structure of the stent is composed of wires which have different shape memories.

The method according to the present invention is characterized in that the stent is subjected over at least portions thereof to a specific application of heat or cold in order to influence the restoring force and/or the geometric shape.

At the core of the invention is the measure of using wires having different shape memories in the support structure of a stent. Such alloys are usually formed from a combination of the two metals nickel and titanium (nitinol). At a low temperature, this material has a compressed structure. However, the material expands when a limiting temperature is exceeded. The desired limiting conditions can be adjusted by an appropriate selection of the alloy components.

Such a wire has hysteresis behavior, i.e., the wire changes from the martensitic state to the austenitic state at a defined first transition temperature. The wire maintains this state until its temperature is cooled below a second transition temperature which is also defined. The wire then returns into the soft, deformable, martensitic state. This process can be repeated as often as desired. A temperature difference of several degrees exists between the first or upper transition point or temperature and the second or lower transition point or temperature. This is called hysteresis.

In accordance with the present invention, wires are arranged in the support structure which change from the martensitic state into the austenitic state at different temperatures. Since a hysteresis of several degrees occurs in this case, a support structure can be obtained which can produce different restoring forces, for example, by the application of heat in the physiological range. It is also possible to change the entire geometric shape of a stent or only a portion of the geometric shape of a stent. Thus, a stent can be made available which expands to a greater extent at the ends than in the middle portion. This makes it possible to secure a stent in a body tube.

In accordance with another feature of the present invention, the support structure is divided into at least two length portions, wherein each length portion is composed of wires having different shape memories.

The arrangement of the wires in the support structure is selected in accordance with the properties which the stent is desired to have. Thus, wires having a different shape memory function can be arranged alternatingly in the support structure. However, it is also possible to arrange the wires having different shape memories in groups.

Consequently, it is possible to stiffen a stent only in a certain length area or to additionally stiffen it in a certain length area.

For example, it is an advantage to stiffen an esophagus prosthesis by a stent only in the length portion in which a tumor is located, while permitting peristalsis in other areas. When the tumor changes through growth, so that it interferes with a longer portion of the esophagus, a correspondingly longer portion of the prosthesis or stent can be stiffened and/or this portion can be equipped with a higher restoring force. However, when the tumor recedes, it would be desirable to reduce the restoring force.

A stent may be composed of alternating rows of wires of nitinol, wherein the transition into the austenitic state occurs in one group of wires at 35° C. and in the other group of wires at 41° C. At room temperature, the stent is small, plastic and inelastic. After the stent is placed in the body, the stent is heated to body temperature of approximately 37° C. The stent unfolds or expands as a result of the restoring forces of the first group of nitinol wires. If necessary, the other nitinol wires can also be changed over by the application of heat, so that the wires change over into the austenitic state. This doubles the restoring force of the entire stent.

The application of heat can be effected by a balloon with warm water. The application of heat can also be effected by electric current or by microwaves. Only when cold is applied to below the hysteresis point, for example, by the application of ice water, so that a heat removal takes place, the restoring force is lowered again.

The stent can remain in the body and can be unfolded or expanded as desired. However, such a stent can also be easily removed from the body.

In accordance with another feature of the present invention, wires with different shape memories can be arranged distributed in circumferential direction of the support structure. For example, a stent may be manufactured from three different nitinols. By utilizing a balloon catheter through which liquid can flow and which preferably has a temperature control, it is then possible to adjust the restoring force of the stent in three gradations at any location of the stent. This is completely reversible by the application of cold.

Various configurations of the support structure can be provided in a stent. The wires may be linked in the support structure, or the wires may be connected to each other in another suitable manner. The wires which have a defined transition temperature and a hysteresis behavior may be of metal alloys. However, the wires may also be of synthetic material.

In accordance with a further development of the present invention, the support structure of the stent may be embedded in a casing of elastomer. The elastomer specifically may be a memory elastomer. A memory elastomer is a temperature-dependent elastomer which is hard and small in the cold state. Consequently, the stent can be easily placed in a body tube. The stent only expands when it is heated to body temperature or slightly below body temperature.

The support structure can also be composed of individual clamp-like wire clasps which are arranged one behind the other. Such clamp-like clasps extend partially around the circumference of the stent. The clasps are advantageously arranged offset relative to each other. The individual clamp-like clasps are of different nitinols and are cast in silicone.

The method according to the present invention for changing the configuration of a stent placed in a body tube is carried out by influencing the stent with respect to its restoring force and/or its geometric shape at least over portions thereof by a specific application of heat or cold.

Consequently, it is possible to influence with the medically required precision exactly those areas of the stent in which a transition is to take place.

In accordance with a preferred feature, the heat or cold application is effected by means of a balloon catheter with temperature monitoring and/or temperature control. The balloon catheter is constructed in such a way that it has zones of changeable temperature over the length thereof. In this manner, it is possible to carry out a specific heat or cold application in certain areas of the stent.

The various features of novelty which characterize the invention are pointed out with particularity in the claims annexed to and forming a part of the disclosure. For a better understanding of the invention, its operating advantages, specific objects attained by its use, reference should be had to the drawing and descriptive matter in which there are illustrated and described preferred embodiments of the invention.

BRIEF DESCRIPTION OF THE DRAWING In the drawing.

DETAILED DESCRIPTION OF THE PREFERRED EMBODIMENTS

Figure 1:
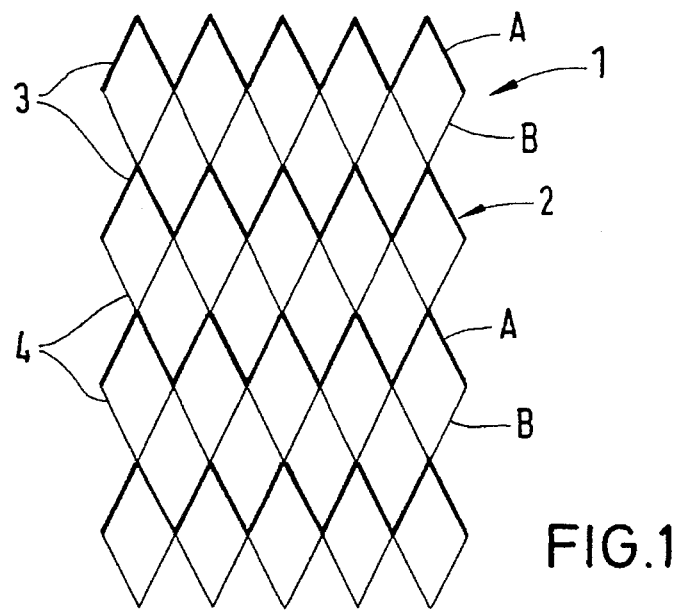
FIG. 1 is a developed view of a stent according to the present invention.

FIG. 1 of the drawing is a developed view of a stent 1 with a support structure 2 which is composed of wires 3 and 4 arranged in a zigzag configuration.

The wires 3 are of a nitinol with hysteresis behavior and a defined transition temperature of 35° C., while the wires 4 are of a nitinol with a transition temperature of 40° C. In this manner, the stent 1 has individual rings A,B with different shape memories.

The rings A and B are shown in FIG. 1 by lines of different thicknesses.

Depending on the transition temperature, the rings A and B change over into the austenitic state. At room temperature, the stent 1 is small and plastic, but inelastic. After the stent 1 is placed in a body tube, the stent 1 expands at room temperature as a result of the change in the state of the rings A. Subsequently, the rings A maintain their state.

If necessary, the rings B can also be unfolded or expanded. This is effected by the application of heat. This causes a doubling of the restoring force of the entire stent 1. An application of heat can also be carried out specifically targeted to only individual rings B in order to produce an expansion of the rings B only in these areas.

Figure 2:
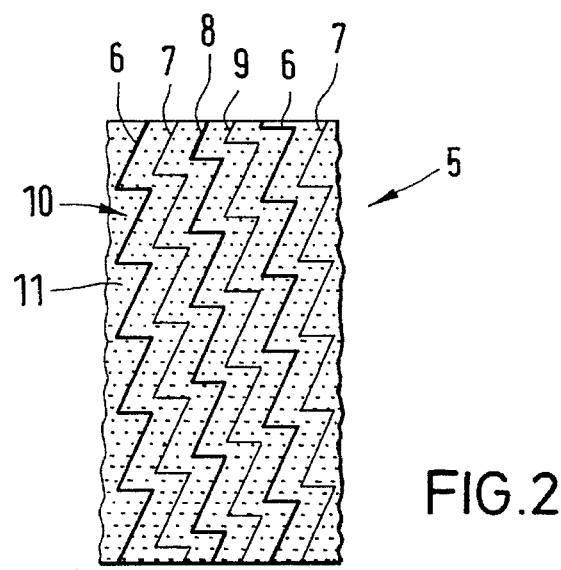
FIG. 2 is a developed view of another embodiment of the stent according to the present invention.

FIG. 2 shows a part of a stent 5 in which wires 6–9 with different shape memories are arranged in circumferential direction of the support structure 10. The support structure 10 is embedded in a casing 11 of an elastomer.

The wires 6–9 are composed of different alloys whose transition temperatures are 35° C., 38° C., 40° C. and 42° C., respectively, and which have hysteresis behavior. In this manner, it is possible to adjust the restoring force in four gradations. This is effected by a specific heat application. The process is completely reversible by the application of cold.

Figure 3:
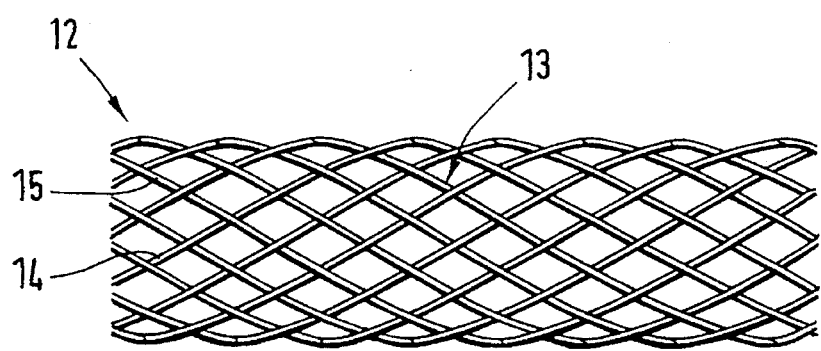
FIG. 3 shows another embodiment of a stent.

The stent shown in FIG. 3 has a braided support structure 13.

The support structure 13 is composed of plastic wires 14, 15 with shape memories. The plastic wires 14, 15 also have a defined transition temperature and have hysteresis behavior.

The invention is not limited by the embodiments described above which are presented as examples only but can be modified in various ways within the scope of protection defined by the appended patent claims.

I claim:

1. A stent for placement in a body tube, the stent comprising a flexible support structure, the support structure comprising at least two groups of wires meshed together, wherein the at least two groups of wires are of a material having shape memory, and wherein the shape memory of the material of one group of wires is different from the shape memory of another group of wires.

2. The stent according to claim 1, wherein the support structure has at least two length portions, wherein the shape memory of the material of the wires of one length portion is different from the shape memory of the material of the wires of another length portion.

3. The stent according to claim 1, comprising wires of materials having different shape memories distributed in a circumferential direction of the support structure.

4. The stent according to claim 1, wherein the wires are of a shape memory alloy having a defined transition temperature and hysteresis behavior.

5. The stent according to claim 4, wherein the wires are of nitinol.

6. The stent according to claim 1, wherein the wires are of a synthetic shape memory material having a defined transition temperature and hysteresis behavior.

7. A stent for placement in a body tube, comprising a casing of elastomer, and at least two groups of wires embedded in the casing, wherein the at least two groups of wires are of a material having shape memory, and wherein the shape memory of the material of one group of wires is different from the shape memory of another group of wires.

8. The stent according to claim 7, wherein the elastomer is a memory elastomer.

9. A method for changing a configuration of a stent placed in a body tube, the stent being composed of at least two groups of wires of materials having different shape memories, the method comprising influencing at least one of a restoring force and a geometric shape of the stent by carrying out a specific application of one of heat and cold at least at portions of the stent.

10. The method according to claim 9, comprising carrying out the application of heat or cold by a balloon catheter having at least one of temperature monitoring and temperature control.

* * * * *